(12) United States Patent
Vicario et al.

(10) Patent No.: US 11,191,441 B2
(45) Date of Patent: Dec. 7, 2021

(54) SIMULTANEOUS ESTIMATION OF RESPIRATORY MECHANICS AND PATIENT EFFORT VIA PARAMETRIC OPTIMIZATION

(71) Applicant: KONINKLIJKE PHILIPS N.V., Eindhoven (NL)

(72) Inventors: Francesco Vicario, Boston, MA (US); Antonio Albanese, New York, NY (US); Dong Wang, Scarsdale, NY (US); Nikolaos Karamolegkos, New York, NY (US); Nicolas Wadih Chbat, White Plains, NY (US)

(73) Assignee: Koninklijke Philips N.V., Eindhoven (NL)

( * ) Notice: Subject to any disclaimer, the term of this patent is extended or adjusted under 35 U.S.C. 154(b) by 566 days.

(21) Appl. No.: 15/763,876

(22) PCT Filed: Sep. 18, 2016

(86) PCT No.: PCT/IB2016/055568
§ 371 (c)(1),
(2) Date: Mar. 28, 2018

(87) PCT Pub. No.: WO2017/055959
PCT Pub. Date: Apr. 6, 2017

(65) Prior Publication Data
US 2018/0279963 A1 Oct. 4, 2018

Related U.S. Application Data

(60) Provisional application No. 62/234,106, filed on Sep. 29, 2015.

(51) Int. Cl.
*A61B 5/03* (2006.01)
*A61B 5/085* (2006.01)
(Continued)

(52) U.S. Cl.
CPC .............. *A61B 5/038* (2013.01); *A61B 5/085* (2013.01); *A61B 5/087* (2013.01); *A61B 5/0816* (2013.01);
(Continued)

(58) Field of Classification Search
USPC ....................................................... 600/533
See application file for complete search history.

(56) References Cited

U.S. PATENT DOCUMENTS 6,435,182 B1  8/2002 Lutchen et al.
2003/0010339 A1* 1/2003 Banner ............. A61M 16/0051
128/204.18

(Continued)

FOREIGN PATENT DOCUMENTS

EP  0521515 B1  10/1996
EP  0904730 A1  3/1999
(Continued)

OTHER PUBLICATIONS

Yukitake et al. (Effect of Respiratory Inertance on Elastance and Resistance Measurements Using Multiple Linear Regression Analysis during Mechanical Ventilation, Med. Bull. Fukuoka Univ., vol. 26(4), pp. 199-204, 1999 (Year: 1999).*

(Continued)

*Primary Examiner* — Jacqueline Cheng
*Assistant Examiner* — Tho Q Tran
(74) *Attorney, Agent, or Firm* — Daniel H. Brean (57) ABSTRACT

Respiratory variables are estimated on a per-breath basis from airway pressure and flow data acquired by airway pressure and flow sensors (20, 22). A breath detector (28) detects a breath interval. A per-breath respiratory variables estimator (30) fits the airway pressure and flow data over the detected breath interval to an equation of motion of the lungs relating airway pressure, airway flow, and a single-breath (Continued)

parameterized respiratory muscle pressure profile (40, 42) to generate optimized parameter values for the single-breath parameterized respiratory muscle pressure profile. Respiratory muscle pressure is estimated as a function of time over the detected breath interval as the single-breath parameterized respiratory muscle pressure profile with the optimized parameter values, and may for example be displayed as a trend line on a display device (26, 36) or integrated (32) to generate Work of Breathing (WoB) for use in adjusting settings of a ventilator (10).

13 Claims, 3 Drawing Sheets

(51) Int. Cl.
  *A61B 5/087* (2006.01)
  *G16H 50/50* (2018.01)
  *G16H 50/20* (2018.01)
  *A61B 5/08* (2006.01)
  *A61B 5/00* (2006.01)
  *A61B 5/091* (2006.01)
  *G16H 40/63* (2018.01)
  *G16H 20/40* (2018.01)

(52) U.S. Cl.
  CPC ............ *A61B 5/091* (2013.01); *A61B 5/7242* (2013.01); *A61B 5/7275* (2013.01); *G16H 40/63* (2018.01); *G16H 50/20* (2018.01); *G16H 50/50* (2018.01); *A61B 5/682* (2013.01); *A61B 2505/03* (2013.01); *G16H 20/40* (2018.01)

(56) References Cited

U.S. PATENT DOCUMENTS

| | | |
|---|---|---|
| 2010/0071696 A1 | 3/2010 | Jafari |
| 2010/0307499 A1 | 12/2010 | Eger et al. |
| 2014/0276173 A1 | 9/2014 | Banner et al. |
| 2014/0283833 A1 | 9/2014 | Zheng et al. |
| 2014/0350429 A1 | 11/2014 | Truschel et al. |
| 2014/0373845 A1 | 12/2014 | Dong |

FOREIGN PATENT DOCUMENTS

| | | |
|---|---|---|
| EP | 1972274 A1 | 9/2008 |
| WO | 0183014 A2 | 11/2001 |
| WO | 2010067244 A1 | 6/2010 |

OTHER PUBLICATIONS

Vicario, F. et al., "Noninvasive Estimation of Respiratory Mechanics in Spontaneously Breathing Ventilated Patients: A Constrained Optimization Approach." IEEE Transactions on Biomedical Engineering. TBME-00458-2015.R1.

* cited by examiner

SIMULTANEOUS ESTIMATION OF RESPIRATORY MECHANICS AND PATIENT EFFORT VIA PARAMETRIC OPTIMIZATION

CROSS-REFERENCE TO PRIOR APPLICATIONS

This application is the U.S. National Phase application under 35 U.S.C. § 371 of International Application No. PCT/IB2016/055568, filed on Sep. 18, 2016, which claims the benefit of U.S. Provisional Patent Application No. 62/234,106, filed on Sep. 29, 2015. These applications are hereby incorporated by reference herein.

FIELD

The following relates generally to the respiratory arts, respiratory monitoring arts, and related arts such as mechanical ventilation arts.

BACKGROUND

Clinical assessment of the respiratory system may be performed on a quantitative basis by estimating certain respiratory values, e.g. respiratory muscle pressure, respiratory system resistance, and respiratory system compliance or elastance.

The respiratory muscle pressure, typically denoted as $P_{mus}(t)$, is a (negative) pressure applied by the patient during respiration. More particularly, during inspiration the thoracic diaphragm operates to expand the volume of the lungs, thus reducing pressure for a given volume of air (as in the case of a blocked airway) or drawing air into the lungs (in the case of normal inhalation). Respiratory muscle pressure is a useful metric for respiratory monitoring generally as it is a metric of spontaneous breathing effort by the patient. Estimating $P_{mus}(t)$ is of particular value in conjunction with mechanical ventilation support modes such as Pressure Support Ventilation (PSV) in which the patient and the mechanical ventilator share the mechanical work performed on the respiratory system. Usually the goal is to provide minimal mechanical ventilation that is sufficient to achieve efficient respiration without fatiguing the patient. Quantitative assessment of $P_{mus}(t)$ can therefore be used to select the appropriate level of ventilation support delivered by the ventilator in order to prevent both atrophy and fatigue of patient respiratory muscles.

The clinical parameter commonly used to assess the effort made by the patient is known as Power of Breathing (PoB) or Work of Breathing (WoB). The PoB can be computed from an estimate of $P_{mus}(t)$ by integration, i.e.:

$$PoB = \frac{1}{T}\int_T P_{mus}(t)dt \quad (1)$$

where T is some chosen time interval preferably encompassing several breaths. PoB is measured in units of power or energy per unit time, e.g. Joules/minute. Work of breathing is similar, except the integration time interval T in Equation (1) is defined for WoB as a single breath (or the inspiratory period of a breath since $P_{mus}(t)=0$ may be assumed for expiration). WoB is thus in units of energy/ breath, e.g. Joules/breath. One complication of WoB is that breath duration can in general vary from breath to breath.

The respiratory muscle pressure, $P_{mus}(t)$, may be measured invasively, for example by measuring the esophageal pressure ($P_{es}$) via insertion of a balloon-tipped catheter in the patient's esophagus. In this approach, the measured $P_{es}(t)$ is assumed to be a good proxy for the pleural pressure ($P_{pl}$) and can be used, in conjunction with an estimate of chest wall compliance $C_{rs}$ (or elastance $E_{rs}=1/C_{rs}$), to compute the WoB via the so-called Campbell diagram or, equivalently, via explicit computation of $P_{mus}(t)$ and then of WoB via Equation (1) with time interval T being one breath or inspiration period. Invasive measurement of $P_{mus}(t)$ can be problematic since techniques involving airway blockage can stress the patient (who is usually already in a weakened state due to some sort of respiratory distress). Furthermore, invasive estimates of $P_{in}(t)$ are generally based on assumptions that may be unrealistic in practice or are performed in abnormal breathing states (e.g. with the airway blocked) so that the estimated $P_{mus}(t)$ may be different from that exerted by the patient during normal respiration.

Respiratory system resistance ($R_{rs}$) and compliance ($C_{rs}$) or elastance ($E_{rs}$) provide quantitative information about the mechanical properties of the patient's respiratory system. These respiratory system values can be used to diagnose respiratory diseases and/or to inform selection of appropriate mechanical ventilation modalities and/or therapeutic paths. Estimation of respiratory system resistance and compliance (or elastance) can be performed by applying the flow-interrupter technique (also called End Inspiratory Pause, EIP). However, this is an invasive technique that interferes with the therapeutic mechanical ventilation pattern that provides life-sustaining respiration to the patient.

The following discloses a new and improved systems and methods that address the above referenced issues, and others.

SUMMARY

In one disclosed aspect, a respiratory monitor device is disclosed. An airway pressure sensor is configured to acquire airway pressure data as a function of time, and an airway flow sensor is configured to acquire airway flow data as a function of time. A breath detector comprises an electronic processor programmed to detect a breath interval in at least one of the airway pressure data and the airway flow data. A per-breath respiratory variables estimator comprises an electronic processor programmed to estimate respiratory muscle pressure as a function of time over the detected breath interval by operations including: fitting the airway pressure and airway flow data over the breath interval to an equation of motion of the lungs relating airway pressure, airway flow, and a single-breath parameterized respiratory muscle pressure profile to generate optimized parameter values for the single-breath parameterized respiratory muscle pressure profile; and estimating the respiratory muscle pressure as a function of time over the detected breath interval as the single-breath parameterized respiratory muscle pressure profile with the optimized parameter values. In some embodiments the per-breath respiratory variables estimator is programmed to fit the airway pressure and airway flow data over the breath interval to the equation of motion of the lungs by performing least squares optimization of a linear problem $\overline{P}_{aw}=M\overline{X}$ where $\overline{P}_{aw}$ is a vector of the airway pressure data over the breath interval, $\overline{X}$ is a parameters vector that includes the parameters that are optimized by the fitting, and M is a connecting matrix. The parameters vector $\overline{X}$ may further include at least one respiratory resistance parameter and at least one respiratory compliance or elastance parameter, and in some embodiments further includes a respiratory inertance parameter.

In another disclosed aspect, a non-transitory storage medium stores instructions executable by an electronic processor to perform a per-breath respiratory variables estimation method operating on airway pressure data and airway flow data. The method includes the step of detecting a breath interval in at least one of the airway pressure data and the airway flow data, the step of fitting the airway pressure and airway flow data over the breath interval to an equation of motion of the lungs relating airway pressure, airway flow, and a single-breath parameterized respiratory muscle pressure profile (40, 42) to generate optimized parameter values for the single-breath parameterized respiratory muscle pressure profile, and the step of estimating the respiratory muscle pressure as a function of time over the detected breath interval as the single-breath parameterized respiratory muscle pressure profile with the optimized parameter values. In some embodiments, the single-breath parameterized respiratory muscle pressure profile has a downward portion extending from an initial pressure at the beginning of the breath interval to a negative pressure of largest magnitude at a first time $T_p$, an upward portion extending from the first time $T_p$ to a second time $T_e$ and a flat portion extending from the second time $T_e$ to the end of the breath interval. In such embodiments, the fitting may employ a linear matrix equation to generate optimized parameter values for parameters of the single-breath parameterized respiratory muscle pressure profile including the initial pressure $P_0$ at the beginning of the breath interval, the negative pressure $P_p$ of largest magnitude at the first time $T_p$, and a pressure $P_e$ at the second time $T_e$. To facilitate evaluating as a linear problem, in some embodiments the fitting employing the linear matrix equation does not fit any time parameters of the respiratory muscle pressure profile.

One advantage resides in providing estimation of respiratory effort on a per-breath basis.

Another advantage resides in providing estimation of respiratory effort that is robust against high frequency noise during inspiration.

Another advantage resides in providing Work of Breathing (WoB) or Power of Breathing (PoB) estimates for a spontaneously breathing patient with improved accuracy for use in setting an appropriate level of mechanical ventilation support.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

In approaches disclosed herein, the respiratory muscle pressure $P_{mus}(t)$, respiratory system resistance $R_{rs}$, and respiratory system compliance C or elastance $E_{rs}=1/C_{rs}$ are simultaneously estimated on a per-breath basis by evaluating the Equation of Motion of the Lungs:

$$P_{aw}(t) = R_{rs}\dot{V}(t) + \left(\frac{1}{C_{rs}}\right)V(t) + P_{mus}(t) + P_{baseline} \quad (2)$$

where $P_{aw}(t)$ is the measured airway pressure, $\dot{V}(t)$ is the measured airway flow, V(t) is the respired air volume, i.e. $V(t)=\int\dot{V}(t)dt$, and $P_{baseline}$ is a constant. In performing this simultaneous estimation, the airway pressure $P_{aw}(t)$ and airway flow $\dot{V}(t)$ are sampled. Evaluating N samples entails solving for N+2 unknowns (including N values of $P_{mus}(t)$ and the values of $R_{rs}$ and $C_{rs}$). This is an underdetermined problem as the number of data points (N) is less than the number of unknowns (N+2).

Beyond the problem being underdetermined, a further difficulty recognized herein is that the measured airway pressure $P_{aw}(t)$ and airway flow $\dot{V}(t)$ are likely to be noisy, especially during inhalation which is a rapidly changing transient phase. It is this noisy transient inhalation phase that is of greatest interest in estimating the respiratory muscle pressure $P_{mus}(t)$, since it is during inhalation that the respiratory muscle pressure is expected to be non-zero in a spontaneously respiring patient.

Approaches disclosed herein advantageously leverage known physiological constraints on the motion of the lungs. First, in a spontaneously breathing patient the motion is expected to follow the breathing cycle. This remains true when the patient is on mechanical ventilation in a support mode such as Pressure Support Ventilation (PSV) in which the ventilator pressure is triggered by the onset of inhalation by the patient. Second, the respiratory muscle pressure $P_{mus}(t)$ is expected to have a certain profile, in particular starting at a baseline value at the onset of inhalation and decreasing (i.e. becoming more negative) until reaching some (negative) peak value, followed by a rapid return back to the baseline value at the end of the breath intake. After the breath intake is complete, $P_{mus}(t)$ is expected to remain close to the baseline pressure for the remainder of the breath (e.g. during the expiration period). While some real deviations from this general profile may be present in a particular breath cycle if the patient has ragged or otherwise unstable breathing, high frequency deviations from this general profile (that is, deviations at frequencies much higher than the respiratory rate) are more likely to be due to measurement noise which should be random and average out to close to zero over the breath.

The approaches disclosed herein leverage these constraints by fitting the measured ($P_{aw}(t)$, $\dot{V}(t)$) samples over a single breath using a single-breath parameterized profile representation of the respiratory muscle pressure $P_{mus}(t)$. By suitable selection of the parameters of this profile, the resulting problem is a linear problem that can be solved by techniques such as gradient descent, Marquardt-Levenberg, or similar least squares optimization. Parameters that would introduce non-linearity into the optimization problem can also be incorporated into the profile, but these parameters are optimized using a grid search. In practice, these parameters that would introduce non-linearity are time parameters (e.g. the time to peak negative value over the breath intake and the breath intake end time).

Furthermore, the single-breath parameterized respiratory muscle pressure profile can absorb the baseline pressure $P_{baseline}$ of the Equation of Motion of the Lungs (Equation (2)). To accommodate the possibility of a gradual drift of $P_{baseline}$ over the breath, the illustrative single-breath parameterized respiratory muscle pressure profiles disclosed herein include different effective baseline values $P_0$ and $P_e$ at the beginning and end of the breath intake, respectfully. The resulting modified Equation of Motion of the Lungs can be written as:

$$P_{aw}(t) = R_{rs}\dot{V}(t) + \left(\frac{1}{C_{rs}}\right)V(t) + [P_{mus,profile}(t, P_0, P_p, P_e)]_{T_p,T_e} \quad (3)$$

where $P_{mus,profile}(t, P_0, P_p, P_e)$ is the single-breath parameterized respiratory muscle pressure profile. The least squares optimization optimizes the pressure parameters $P_0$, $P_p$, $P_e$. These pressure parameters are the baseline pressure $P_0$ at the beginning of the breath intake, the maximum negative pressure $P_p$ reached during the breath intake, and the baseline pressure $P_e$ at the end of the breath intake. Typically, $P_0 \cong P_e$ is expected, but some difference between these values may be obtained by the least squares fitting, which accounts for any gradual drift in the baseline pressure $P_{baseline}$ of Equation (2) over time. The notation $[\ldots]_{T_p,T_e}$ denotes that Equation (3) is evaluated with fixed values for time parameters $T_p$ and $T_e$. The time parameter $T_p$ is the time at which the profile reaches the peak negative pressure $P_p$, and the time parameter $T_e$ is the time at which the profile returns to the baseline pressure $P_e$. Incorporating the time parameters $T_p$ and $T_e$ into the least squares fit would result in a non-linear problem which is much more computationally difficult to solve. Accordingly, in illustrative examples herein the time parameters $T_p$ and $T_e$ are fitted using a grid search, that is, Equation (3) is optimized for several possible $(T_n, T_e)$ pairs and the optimization yielding the best fit to the measured $(P_{aw}(t), \dot{V}(t))$ samples over the fitted breath are selected.

Advantageously, the least squares fit of Equation (3) to the measured $(P_{aw}(t), \dot{V}(t))$ samples over the fitted breath entails fitting only five parameters: $R_{rs}$, $C_{rs}$, $P_0$, $P_p$, and $P_e$. If the sampling rate is one sample every 10 milliseconds and the breath is of duration 3 seconds, the data set includes N=300 samples, so that the problem is now highly overdetermined. Rapid convergence is also facilitated by employing physically realistic starting values for the parameters—for example some suitable starting parameters may be $P_0 = P_e = 0$ or $P_0 = P_e = P_{avg}$ where $P_{avg}$ is the average pressure during the expiration phase. Suitable starting values for the remaining parameters may be chosen as typical literature values for the type of patient being monitored. Other choices for initializing the parameter values are also contemplated. Because this five-parameter fit is fast, it is feasible to repeat the optimization for several possible $(T_p, T_e)$ pairs in the time frame of a single breath (typically 3-5 seconds per breath for a healthy adult with a respiration rate in the range 12-20 breaths per minute) and select the optimization with the lowest fitting error. Thus, the output latency is on the order of a single breath or less, i.e. 5 seconds or less in some embodiments. This low latency is sufficient to enable approximately real-time trending of the parameters of interest, including: $P_{mus}(t)$ estimated as the optimally fitted profile $[P_{mus,profile}(t, P_0, P_p, P_e)]_{T_p,T_e}$ and the respiratory system parameters $R_{rs}$ and $C_{rs}$ (or $E_{rs}$). This low latency also provides near real-time Work of Breathing (WoB) or Power of Breathing (PoB) by evaluation of Equation (1). For WoB which is computed over a single breath, it is contemplated to analytically compute the closed-form integral of $[P_{mus,profile}(t, P_0, P_p, P_e)]_{T_p,T_e}$ parameterized by the parameters $(P_0, P_p, P_e, T_p, T_e)$ so that evaluation of the integral of Equation (1) reduces to evaluating an algebraic formula of the form WoB $(P_0, P_p, P_e, T_p, T_e)$.

Figure 1:
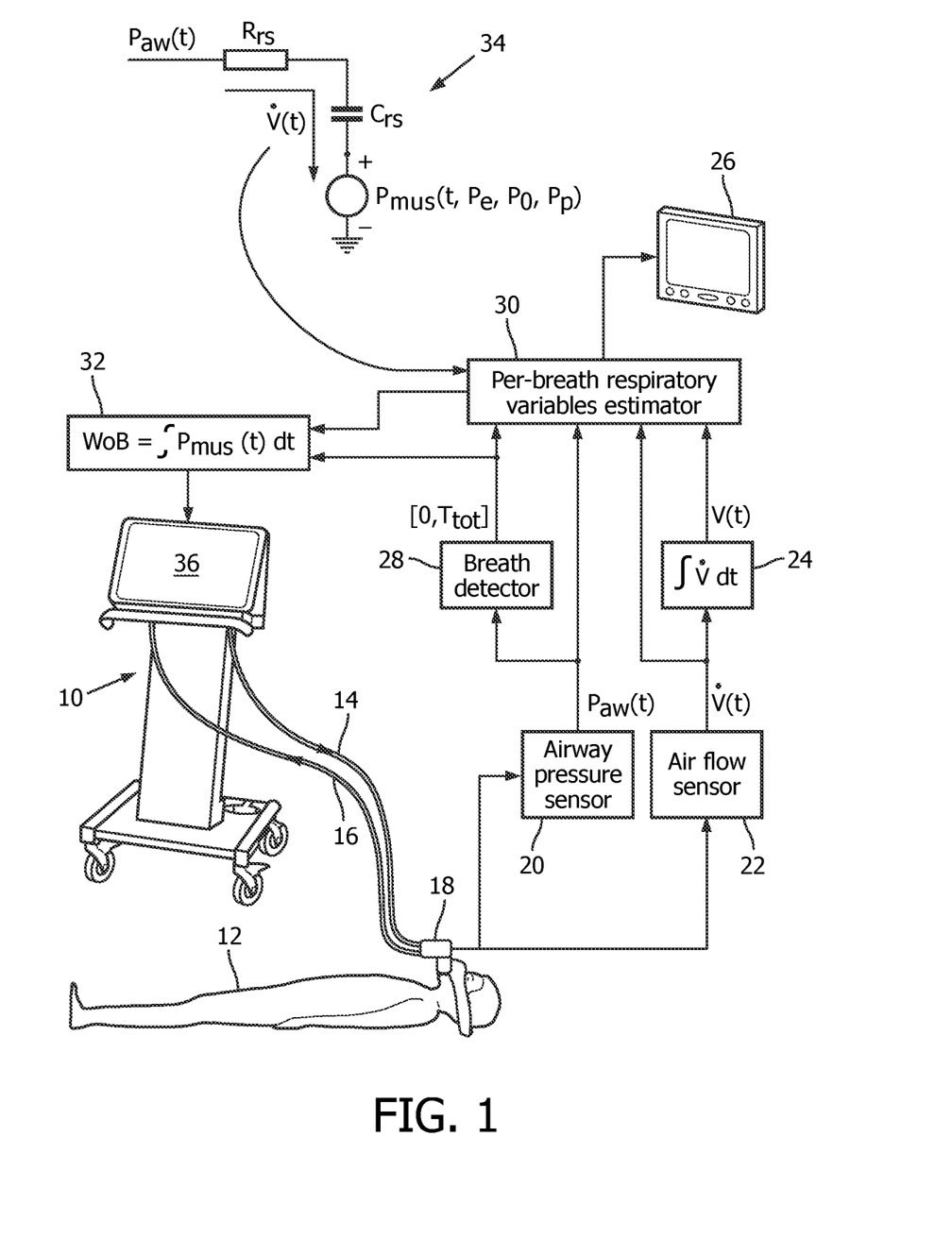
FIG. 1 diagrammatically illustrates a respiratory variables estimation system in combination with illustrative applications thereof including a patient monitor and a mechanical ventilator.

With reference now to FIG. 1, a respiratory parameters estimation system employing the above principles is described, in combination with illustrative patient monitor and mechanical ventilator setting applications thereof. A mechanical ventilator 10 is providing mechanical ventilation of a patient 12 in a support mode, such as Pressure Support Ventilation (PSV), in which the patient 12 is spontaneously breathing. The mechanical ventilator 10 delivers pressurized air to the patient via an inlet air hose 14 and expired air returns to the ventilator 10 via an outlet air hose 16. Coupling of air to and from the patient is via a suitable patient accessory 18, such as a full-face mask or a tracheal tube.

As diagrammatically indicated in FIG. 1, the air flow circuit includes an airway pressure sensor 20 that measures (i.e. samples) the airway pressure $P_{aw}(t)$, and an airway flow sensor 22 that measures the airway flow $\dot{V}(t)$. In the case of non-invasive ventilation, for which air leaks are sometimes present, the airway flow $\dot{V}(t)$ may optionally be corrected for air leaks using a leak estimation algorithm. An integrator 24 computes the air volume $V(t) = \int \dot{V}(t)dt$. Further, because the respiratory variables estimation approaches disclosed herein operate on a per-breath basis, a breath detector 28 is configured to segment the acquired $(P_{aw}(t), \dot{V}(t))$ sample stream into time segments each corresponding to a single breath. In the illustrative embodiment of FIG. 1, the breath detector 28 analyzes the airway pressure samples $P_{aw}(t)$ and may, by way of illustration, detect the onset of inspiration as a characteristic abrupt decrease in $P_{aw}(t)$ indicating the beginning of the intake of a breath. Each successive breath is then defined as the interval from the onset of one inspiration period to the onset of the next inspiration period. Alternatively, the breath detector can analyze the airway flow signal $\dot{V}(t)$ to detect successive breaths, or can analyze both airway pressure and airway flow to detect a breath interval. Each breath identified by the breath analyzer is denoted here as a time interval $[0, T_{tot}]$ where time 0 corresponds to the first sample at the onset of the inspiration period and time $T_{tot}$ corresponds to the end of the breath, that is, the last sample just before the beginning of the next breath detected by the breath detector 28.

A per-breath respiratory variables estimator 30 evaluates Equation (3) or another suitable Equation of Motion of the Lungs for each breath interval $[0, T_{tot}]$ delineated by the breath detector 28 in order to determine the respiratory muscle pressure $P_{mus}(t)$ over the breath interval and the respiratory system resistance R and compliance C or elastance $E_{rs}$. For illustration, an equivalent respiratory circuit 34 of Equation (3) is diagrammatically shown in FIG. 1. The computed respiratory muscle pressure, resistance, and compliance or elastance values may be variously used, for example displayed on the patient or nurses' station monitor 26, and/or processed by a WoB calculator 32 (or alternatively a PoB calculator) in accordance with Equation (1), or so forth. The calculated PoB or WoB may be displayed on a display component 36 of the mechanical ventilator 10, e.g. as a trend line and/or as a current numerical value, for reference by the physician in assessing and optionally adjusting the ventilator setting(s). Automated closed-loop control of these settings based on the calculated PoB or WoB (and possibly other inputs) is also contemplated.

The data acquisition and processing components 20, 22, 24, 28, 30, 32 may be variously arranged in a specific implementation. For example, the airway pressure sensor 20 may be built into the patient accessory 18, while the airway flow sensor 22 may be built into the patient accessory 18 or mounted on one of the air hoses 14, 16 or housed within the mechanical ventilator 10. The data analysis components 24, 28, 30, 32 may be implemented by any electronic data processing device, such as a microcontroller or microprocessor or other electronic processor of the mechanical ventilator 10, and/or a microprocessor or microcontroller or other electronic processor of the patient or nurses' station monitor 26, or so forth. The data processing may be further embodied as a non-transitory storage medium storing instructions readable and executable by an electronic processor to perform the disclosed data processing and other functions (e.g. data acquisition, display device control, et cetera). The non-transitory storage medium may, for example, include a hard disk drive or other magnetic storage medium, and/or an optical disk or other optical storage medium, and/or a flash memory or other electronic storage medium, and/or so forth. To enable electronic data processing of the acquired $P_{aw}(t)$ and $\dot{V}(t)$, these signals are sampled and digitized. The sampling and analog-to-digital (A/D) conversion circuitry may be built into the respective sensors 20, 22, or may be performed by sampling and A/D converters associated with sensor input ports of the mechanical ventilator 10 or patient or nurses' station monitor 26, or so forth these data acquisition and pre-processing or data formatting details are not illustrated in diagrammatic FIG. 1.

Figure 2:
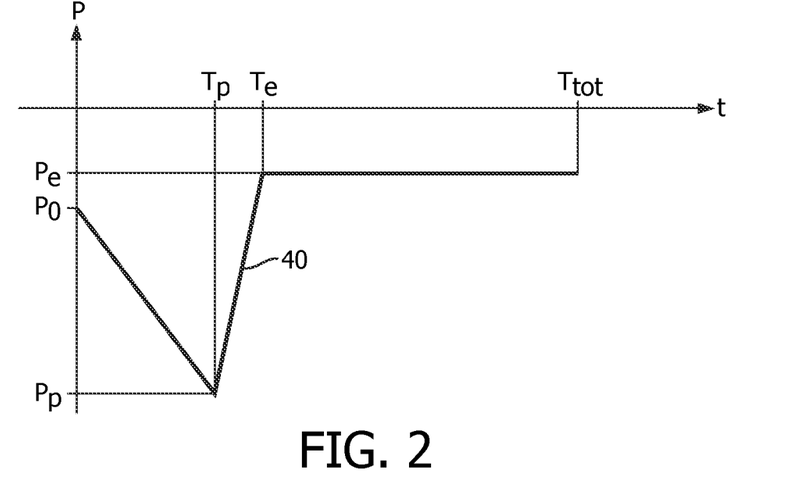
FIG. 2 plots an illustrative single-breath piecewise linear parameterized respiratory muscle pressure versus time breath profile that may be used by the per-breath respiratory variables estimator of FIG. 1.

With continuing reference to FIG. 1 and with further reference to FIG. 2, an illustrative embodiment of the per-breath respiratory variables estimator 30 is described. This illustrative embodiment employs a single-breath piecewise linear parameterized respiratory muscle pressure profile 40 which is illustrated in FIG. 2 and given below:

$$P_{mus,profile}(t) = \begin{cases} P_0\left(1 - \frac{t}{T_p}\right) + P_p\left(\frac{t}{T_p}\right) & \text{for } 0 \le t < T_p \\ P_p\left(1 - \frac{t - T_p}{T_e - T_p}\right) + P_p\left(\frac{t}{T_p}\right) & \text{for } T_p \le t < T_e \\ P_e & \text{for } T_e \le t \le T_{tot} \end{cases} \quad (4)$$

In this illustrative single-breath parameterized respiratory muscle pressure profile 40, the time parameters $T_p$ and $T_e$ are assumed to be known, and the profile assumes that $P_{mus}(t)$ linearly decreases between t=0 and t=$T_p$, linearly increase between t=$T_p$ and t=$T_e$, and stays constant from t=$T_e$ to t=$T_{tot}$. Applying the Equation of Motion of the Lungs of Equation (3) using the respiratory muscle pressure profile $P_{mus,profile}(t, P_0, P_p, P_e)$ of Equation (4) (where again $T_p$ and $T_e$ are taken as fixed values) to a set of measurement samples $(P_{aw}(0), \dot{V}(t)), V(0)), (P_{aw}(1), \dot{V}(1), V(1)), \ldots, (P_{aw}(T_{tot}), \dot{V}(T_{tot}), V(T_{tot}))$ over a single breath yields the following matrix equation:

$$\begin{bmatrix} P_Y(0) \\ \vdots \\ P_Y(T_p - 1) \\ P_Y(T_p) \\ \vdots \\ P_Y(T_e - 1) \\ P_Y(T_e) \\ \vdots \\ P_Y(T_{tot}) \end{bmatrix} = \quad (5)$$

$$\begin{bmatrix} \dot{V}(0) & V(0) & \left(1 - \frac{0}{T_p}\right) & \frac{0}{T_p} & 0 \\ \vdots & \vdots & \vdots & \vdots & \vdots \\ \dot{V}(T_p-1) & V(T_p-1) & \left(1 - \frac{T_p-1}{T_p}\right) & \frac{T_p-1}{T_p} & 0 \\ \dot{V}(T_p) & V(T_p) & 0 & \left(1 - \frac{0}{T_e-T_p}\right) & 1 \\ \vdots & \vdots & & \vdots & \\ \dot{V}(T_e-1) & V(T_e-1) & \vdots & \left(1 - \frac{T_e-1-T_p}{T_e-T_p}\right) & \vdots \\ \dot{V}(T_e) & V(T_e) & \vdots & 0 & \vdots \\ \vdots & \vdots & & & \\ \dot{V}(T_{tot}) & V(T_{tot}) & 0 & 0 & 1 \end{bmatrix} \begin{bmatrix} R \\ E \\ P_0 \\ P_p \\ P_e \end{bmatrix}$$

where in Equation (5) the notation $P_Y$ replaces the airway pressure notation $P_{aw}$ used elsewhere herein (the subscript "Y" indicating the illustrative use of a Y-piece as the patient accessory 18), and respiratory system resistance $R_{rs}$ and elastance $E_{rs}$ are represented by the shortened forms R and E, respectively. Matrix Equation (5) is solved for the parameters vector $[R\ E\ P_0\ P_p\ P_e]^T$ using least squares optimization (e.g. gradient descent, Levenberg-Marquardt, etc), and the respiratory muscle pressure is estimated over the breath interval $[0, T_{tot}]$ using Equation (4) with the optimized values for $P_0$, $P_p$, and $P_e$ and the assumed fixed values for $T_p$ and $T_e$.

Equation (5) is advantageously a linear problem that can be expressed in the form $\overline{Y}=M\overline{X}$ where $\overline{Y}$ is a measurements vector (more particularly, the airway pressure data vector $P_{aw}=[P_{aw}(0)\ P_{aw}(1)\ \ldots\ P_{aw}(T_{tot})]^T$ in Equation (5)), $\overline{X}$ is a parameters vector (more particularly, the parameters vector $[R\ E\ P_0\ P_p\ P_e]^T$ in Equation (5)), and M is a connecting matrix. In principle, $T_p$ and $T_e$ could also be parameters of the least squares optimization. However, the resulting problem would not be a linear problem expressible in the form $\overline{Y}=M\overline{X}$. Thus, in some embodiments no time parameters of the respiratory muscle pressure profile are fitted by the least squares fitting.

In illustrative examples herein, optimization of $T_p$ and $T_e$ is performed by way of a grid search, in which Equation (5) is solved for several different choices of $T_p$ and $T_e$ and the values of $T_p$ and $T_e$ for the best optimization result are chosen. Because there involves only two parameters $T_p$ and $T_e$, and moreover these parameters have a narrow range of physiologically reasonable values. At a minimum, $0<T_p<T_e<T_{tot}$ holds, and these constraints can be further narrowed by taking into account the physiologically reasonable range of the inspiration period over the breath interval $[0, T_{tot}]$.

Figure 3:
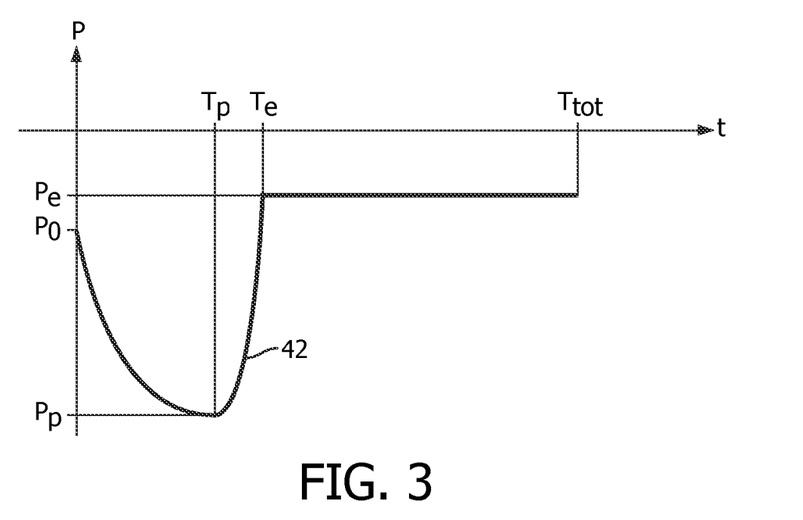
FIG. 3 plots an illustrative single-breath piecewise parabolic parameterized respiratory muscle pressure versus time breath profile that may be used by the per-breath respiratory variables estimator of FIG. 1.

With continuing reference to FIGS. 1 and 2 and further reference to FIG. 3, to provide further improvement in the per-breath respiratory variables estimation, the least squares optimization can also be repeated for two or more different respiratory muscle pressure profile shapes, and the best optimization (that is, the optimization with the lowest fitting error) is chosen. By way of non-limiting illustration, FIG. 3 illustrates a single-breath piece-wise parabolic parameterized respiratory muscle pressure profile 42 in which the interval $[0, T_p)$ is a decreasing parabolic function starting at $P_0$ and ending at $P_p$, the interval $[T_p, T_e)$ is an increasing parabolic function starting at $P_p$ and ending at $P_e$, and the interval $[T_e, T_{tot}]$ has constant value $P_e$. The time parameters $T_p$ and $T_e$ are again assumed to be known, and can be optimized using a grid search. The least squares optimization can also be repeated for different instances of the single-breath parabolic parameterized respiratory muscle pressure profile 42 having different bowing parameters for the two parabolic segments $[0, T_p)$ and $[T_p, T_e)$. Because each least squares minimization with a given profile shape and set of time parameters $T_p$ and $T_e$ is a linear problem of the form $\overline{Y}=M\overline{X}$, a relatively large number of such optimizations (e.g. a dozen or more) can be performed in 1-2 seconds, so that the overall optimization can be completed in the time frame of a single breath. This is repeated on a per-breath basis to generate a continuous waveform $P_{mus}(t)$ with a time latency of less than one breath interval.

In sum, using the linear and parabolic profiles of FIGS. 2 and 3, respectively, the per-breath respiratory variables estimation can be performed as follows: (1) define a set of time pairs $(T_p, T_e)$; (2) for each pair, construct the corresponding least squares optimization problem with piecewise linear and piecewise parabolic profiles (two optimization problems are constructed for each time pair, one using the piecewise linear profile of FIG. 2 and the other using the piecewise quadratic profile of FIG. 3); (3) solve each least squares optimization problem and compute the corresponding sum-of-squares; (4) find the minimum sum-of-squares among all the least squares optimizations; and (5) use the parameters vector $[R\ E\ P_0\ P_p\ P_e]^T$ and the appropriate profile for the solution with the minimum sum-of-squares to compute to estimate $P_{mus}(t)$ and the respiratory system resistance and elastance for the breath. Steps (1)-(5) are repeated for each successive breath.

In some embodiments, the single-breath piece-wise parabolic parameterized respiratory muscle pressure profile has a general shape which includes a downward portion extending from an initial pressure ($P_0$) at the beginning of the breath interval (time t=0) to a negative pressure of largest magnitude ($P_p$) at a first time $T_p$, an upward portion extending from the first time $T_p$ to a second time $T_e$, and a flat portion extending from the second time $T_e$ to the end of the breath interval. This general shape encompasses the shapes of profiles 40, 42 of FIGS. 2 and 3, as well as numerous variants (for example, having a parabolic shape between t=0 and t=$T_p$ and a linear shape between t=$T_p$ and t=$T_e$).

With particular reference to FIG. 1, in the foregoing embodiments the Equation of Motion of the Lungs employed is the first-order form of Equation (2). This models the respiratory system using the equivalent respiratory circuit 34 shown in FIG. 1, which is an RC circuit comprising a resistance and a compliance in series. In other contemplated embodiments, the respiratory system is represented by a more complex equivalent respiratory circuit. For example, the following second-order Equation of Motion of the Lungs:

$$P_{aw}(t) = L\ddot{V}(t) + (R_0 + R_1|\dot{V}(t)|)\dot{V}(t) + \left(\frac{1}{C}\right)V(t) + P_{mus}(t) + P_{baseline} \quad (6)$$

includes a parameter L representing respiratory system inertance, and replaces the single resistance $R_{rc}$ with resistance parameters $R_0$ and $R_1$ characterizing a parabolic resistance. The Equation of Motion of the Lungs of Equation (6) is therefore an equivalent LRC circuit.

Figure 4:
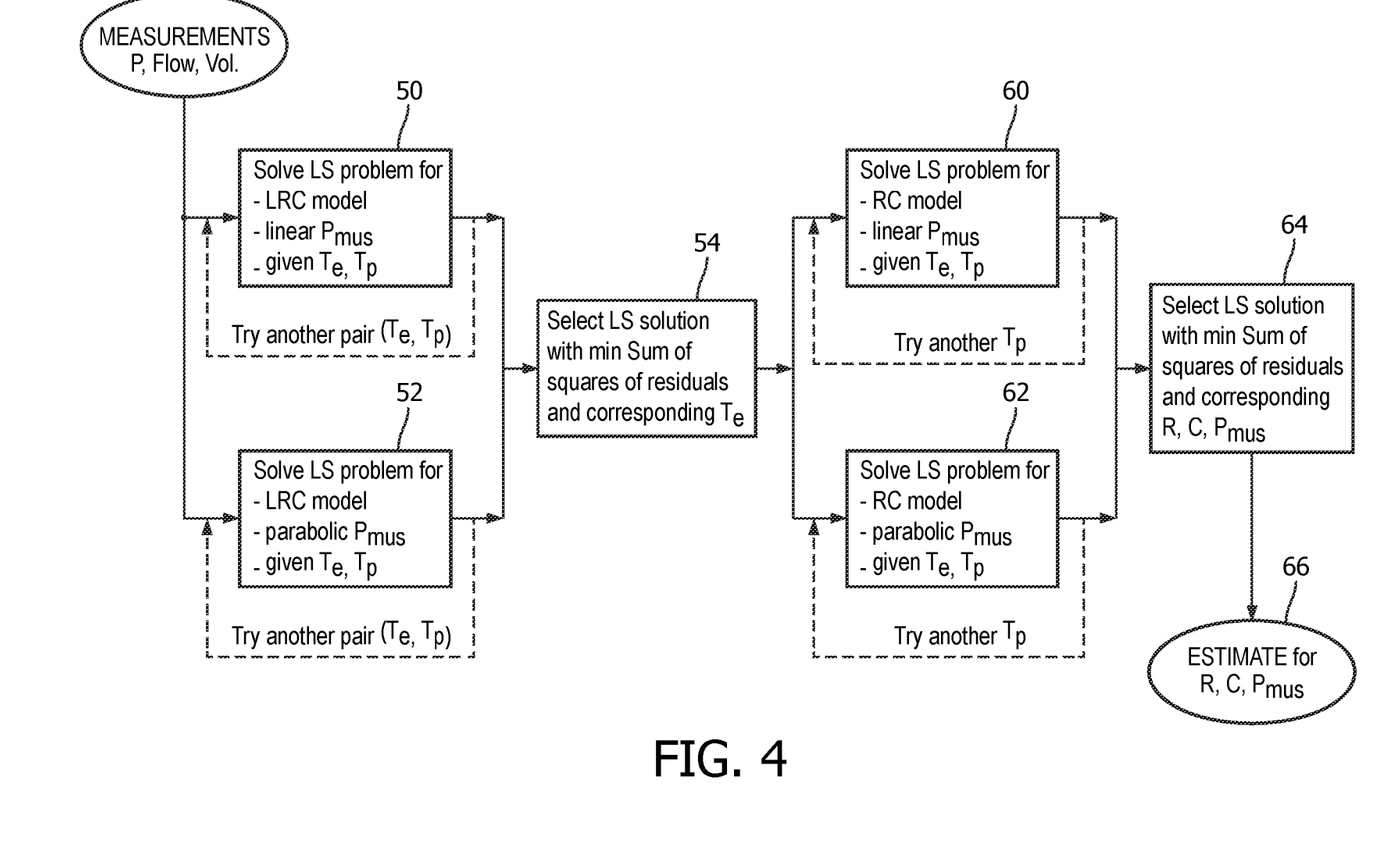
FIG. 4 shows a block diagram of an illustrative process suitably performed by the per-breath respiratory variables estimator of the system of FIG. 1.

With reference to FIG. 4, in one embodiment the second and first order Equations of Motion of the Lungs of respective Equations (6) and (2) are applied in a two-pass approach. In a first pass represented by blocks 50, 52, the LRC circuit of Equation (6) is fitted using the single-breath piecewise linear parameterized respiratory muscle pressure profile 40 of FIG. 2 and several different values for the time parameters pair $(T_p, T_e)$ (block 50), and is fitted using the single-breath piecewise parabolic parameterized respiratory muscle pressure profile 42 of FIG. 3 and several different values for the time parameters pair $(T_p, T_e)$ (block 52). Block 54 selects the least squares (LS) solution with the minimum sum of squares residuals (i.e. lowest fitting error), and sets time parameter $T_e$ to the value of that LS solution with the minimum sum of squares residuals (i.e. lowest fitting error). In a second pass represented by blocks 60, 62, the RC circuit of Equation (2) is fitted using the single-breath piecewise linear parameterized respiratory muscle pressure profile 40 of FIG. 2 and several different values for time parameter $T_p$ (block 60), and is fitted using the single-breath piecewise parabolic parameterized respiratory muscle pressure profile 42 of FIG. 3 and several different values for the time parameter $T_p$ (block 62). In performing the LS optimizations of blocks 60, 62, the time parameter $T_e$ is kept fixed at the value chosen in the block 54. Thereafter, in block 64 the least squares (LS) solution from blocks 60, 62 with the lowest sum of squares residuals is selected, and the set of parameters 66 including $R_{rs}$, $C_{rs}$ (or E), and $P_{mus}(t) \sim P_{mus,profile}(t)$ is generated from the selected LS solution with the minimum sum of squares residuals.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:
1. A respiratory monitor device comprising:
an airway pressure sensor configured to acquire airway pressure data as a function of time;
an airway flow sensor configured to acquire airway flow data as a function of time;
a breath detector comprising an electronic processor programmed to detect a breath interval over a time frame of a single breath, the single breath defined as an interval from an onset of one inspiration period to an onset of a subsequent inspiration period, in at least one of the airway pressure data and the airway flow data;
a per-breath respiratory variables estimator comprising an electronic processor programmed to estimate respiratory muscle pressure as a function of time over the detected breath interval by operations including:

fitting the airway pressure and airway flow data over the breath interval to an equation of motion of the lungs relating airway pressure, airway flow, and a single-breath parameterized respiratory muscle pressure profile to generate optimized parameter values for the single-breath parameterized respiratory muscle pressure profile, and estimating the respiratory muscle pressure as a function of time over the detected breath interval as the single-breath parameterized respiratory muscle pressure profile with the optimized parameter values; and a patient or nurses' station monitor configured to plot a trend line of the respiratory muscle pressure as a function of time estimated by the per-breath respiratory variables estimator for successive breath intervals detected by the breath detector.

2. The respiratory monitor device of claim 1, wherein the per-breath respiratory variables estimator is further programmed to fit the airway pressure and airway flow data over the breath interval to the equation of motion of the lungs by performing least squares optimization of a linear problem $\overline{P}_{aw} = M\overline{X}$ where $\overline{P}_{aw}$ is a vector of the airway pressure data over the breath interval, $\overline{X}$ is a parameters vector that includes the parameters that are optimized by the fitting, and M is a connecting matrix.

3. The respiratory monitor device of claim 2, wherein the parameters vector $\overline{X}$ further includes at least one respiratory resistance parameter and at least one respiratory compliance or elastance parameter.

4. The respiratory monitor device of claim 3, wherein the parameters vector $\overline{X}$ further includes a respiratory inertance parameter.

5. The respiratory monitor device of claim 2, wherein the single-breath parameterized respiratory muscle pressure profile is a single-breath piecewise linear parameterized respiratory muscle pressure profile or a single-breath piecewise parabolic parameterized respiratory muscle pressure profile.

6. The respiratory monitor device of claim 1, wherein the per-breath respiratory variables estimator is programmed to:
fit the airway pressure and airway flow data over the breath interval to a plurality of different equations of motion of the lungs each having a different single-breath parameterized respiratory muscle pressure profile; and
estimate the respiratory muscle pressure as a function of time over the detected breath interval as the single-breath parameterized respiratory muscle pressure profile with the optimized parameter values produced by the best-fitting equation of motion of the lungs.

7. The respiratory monitor device of claim 6, wherein the different single-breath parameterized respiratory muscle pressure profiles include at least one single-breath piecewise linear parameterized respiratory muscle pressure profile and at least one single-breath piecewise parabolic parameterized respiratory muscle pressure profile.

8. The respiratory monitor device of claim 6, wherein the different single-breath parameterized respiratory muscle pressure profiles include single-breath parameterized respiratory muscle pressure profiles with different time parameter values wherein the time parameters are not fitted by the fitting.

9. The respiratory monitor device of claim 1, further comprising:
a mechanical ventilator; and
a work or power of breathing estimator comprising an electronic processor programmed to estimate a power of breathing (PoB) or work of breathing (WoB) by integrating the estimated respiratory muscle pressure as a function of time over the detected breath interval.

10. The respiratory monitor device of claim 1, wherein the single-breath parameterized respiratory muscle pressure profile is $P_{mus,profile}(t, P_0, P_p, P_e)$ where $P_0$ is a fitted parameter representing respiratory muscle pressure at the beginning of the breath interval, $P_p$ is a fitted parameter representing a negative respiratory muscle pressure of maximum magnitude over the breath interval, and $P_e$ is a fitted parameter representing respiratory muscle pressure at the end of the breath interval;

wherein the equation of motion of the lungs is one of:

$$P_{aw}(t) = R_{rs}\dot{V}(t) + \left(\frac{1}{C_{rs}}\right)V(t) + P_{mus,profile}(t, P_0, P_p, P_e) \text{ and } P_{aw}(t) = R_{rs}\dot{V}(t) + E_{rs}V(t) + P_{mus,profile}(t, P_0, P_p, P_e)$$

where $P_{aw}(t)$ represents samples of the airway pressure data, $\dot{V}(t)$ represents samples of the airway flow data, $V(t)$ represents air flow volume computed by integration of airway pressure data, $R_{rs}$ is a fitted parameter representing respiratory system resistance, and either $C_{rs}$ is a fitted parameter representing respiratory system compliance or $E_{rs}$ a fitted parameter representing respiratory system elastance.

11. A method of operating on airway pressure data and airway flow data, the method comprising:
detecting a breath interval over a time frame of a single breath, the single breath defined as an interval from an onset of one inspiration period to an onset of a subsequent inspiration period, in at least one of the airway pressure data and the airway flow data;
fitting the airway pressure and airway flow data over the breath interval to an equation of motion of the lungs relating airway pressure, airway flow, and a single-breath parameterized respiratory muscle pressure profile to generate optimized parameter values for the single-breath parameterized respiratory muscle pressure profile and for respiratory system resistance and for the respiratory system elastance or compliance, and
estimating the respiratory muscle pressure as a function of time over the detected breath interval as the single-breath parameterized respiratory muscle pressure profile with the optimized parameter values;
estimating the respiratory system resistance as the optimized parameter value for the respiratory system resistance;
estimating the respiratory system elastance or compliance as the optimized parameter value for the respiratory system elastance or compliance, wherein the detecting, the fitting, and the estimating operations are performed by an electronic processor;
displaying, on a display device, a trend line representing the estimated respiratory muscle pressure as a function of time;
displaying, on the display device, a trend line representing the respiratory system resistance as a function of time;
displaying, on the display device, a trend line representing the respiratory system elastance or compliance as a function of time.

12. The method of claim 11, wherein the single-breath parameterized respiratory muscle pressure profile has a downward portion extending from an initial pressure at the beginning of the breath interval to a negative pressure of largest magnitude at a first time $T_p$, an upward portion extending from the first time $T_p$ to a second time $T_e$ and a flat portion extending from the second time $T_e$ to the end of the breath interval.

13. The method of claim 11, wherein:
the optimized parameter value for respiratory system resistance includes two resistance parameters $R_0$ and $R_1$; and
the respiratory system resistance is estimated as $R_0 + R_1 |\dot{V}(t)|$.

\* \* \* \* \*